US00PP25258P2

(12) United States Plant Patent
Schaber

(10) Patent No.: US PP25,258 P2
(45) Date of Patent: Jan. 27, 2015

(54) GERANIUM PLANT NAMED 'OGLGER7049'

(50) Latin Name: *Pelargonium×hortorum*
Varietal Denomination: Oglger7049

(71) Applicant: Margaret Schaber, Encinitas, CA (US)

(72) Inventor: Margaret Schaber, Encinitas, CA (US)

(73) Assignee: Dümmen Group B.V., De Lier (NL)

( * ) Notice: Subject to any disclaimer, the term of this patent is extended or adjusted under 35 U.S.C. 154(b) by 94 days.

(21) Appl. No.: 13/815,483

(22) Filed: Mar. 5, 2013

(51) Int. Cl.
*A01H 5/00* (2006.01)

(52) U.S. Cl.
USPC ..... Plt./325

(58) Field of Classification Search
USPC ..... Plt./325
See application file for complete search history.

*Primary Examiner* — Annette Para
(74) *Attorney, Agent, or Firm* — C. A. Whealy

(57) ABSTRACT

A new and distinct cultivar of Zonal Geranium plant named 'Oglger7049', characterized by its upright to outwardly spreading and mounded plant habit; moderately vigorous growth habit; freely branching habit; early and freely flowering habit; and bright red purple-colored flowers held above and beyond the foliar plane on strong peduncles.

1 Drawing Sheet

Botanical designation: *Pelargonium×hortorum*.
Cultivar denomination: 'OGLGER7049'.

BACKGROUND OF THE INVENTION

The present invention relates to a new and distinct cultivar of Zonal Geranium plant, botanically known as *Pelargonium×hortorum*, and hereinafter referred to by the name 'Oglger7049'.

The new Zonal Geranium plant is a product of a planned breeding program conducted by the Inventor in Lompoc, Calif. The objective of the breeding program is to create new moderately vigorous Zonal Geranium plants with attractive flowers.

The new Zonal Geranium plant originated from a cross-pollination made by the Inventor in April, 2006 in Lompoc, Calif. of *Pelargonium×hortorum* 'Pacfox', disclosed in U.S. Plant Pat. No. 18,374, as the female, or seed, parent with *Pelargonium×hortorum* 'Fistangoli', disclosed in U.S. Plant Pat. No. 12,274, as the male, or pollen, parent. The new Zonal Geranium plant was discovered and selected by the Inventor as a single flowering plant from within the progeny of the stated cross-pollination in a controlled greenhouse environment in Lompoc, Calif. in May, 2007.

Asexual reproduction of the new Zonal Geranium plant by vegetative cuttings in a controlled greenhouse environment in Lompoc, Calif. since September, 2007 has shown that the unique features of this new Zonal Geranium plant are stable and reproduced true to type in successive generations.

SUMMARY OF THE INVENTION

Plants of the new Zonal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Oglger7049'.

These characteristics in combination distinguish 'Oglger7049' as a new and distinct Zonal Geranium plant:

1. Upright to outwardly spreading and mounded plant habit.
2. Moderately vigorous growth habit.
3. Freely branching habit.
4. Early and freely flowering habit.
5. Bright red purple-colored flowers held above and beyond the foliar plane on strong peduncles.

Plants of the new Zonal Geranium differ primarily from plants of the female parent, 'Pacfox', in flower color as plants of the new Zonal Geranium have brighter red purple-colored flowers than plants of 'Pacfox'.

Plants of the new Zonal Geranium differ primarily from plants of the male parent, 'Fistangoli', in flower color as plants of 'Fistangoli' have bright purple-colored flowers.

Plants of the new Zonal Geranium can be compared to plants of *Pelargonium×hortorum* 'Oglger4090', disclosed in U.S. Plant Pat. No. 22,044. In side-by-side comparisons conducted in Encinitas, Calif., plants of the new Zonal Geranium differed primarily from plants of 'Oglger4090' in flower color as plants of the new Zonal Geranium had brighter and darker red purple-colored flowers than plants of 'Oglger4090'.

BRIEF DESCRIPTION OF THE PHOTOGRAPHS

The accompanying colored photographs illustrate the overall appearance of the new Zonal Geranium plant showing the colors as true as it is reasonably possible to obtain in colored reproductions of this type. Colors in the photographs may differ slightly from the color values cited in the detailed botanical description which accurately describe the colors of the new Zonal Geranium plant.

The photograph at the bottom of the sheet comprises a side perspective view of a typical flowering plant of 'Oglger7049' grown in a container.

The photograph at the top of the sheet is a close-up view of a typical flowering plant of 'Oglger7049'.

DETAILED BOTANICAL DESCRIPTION

The aforementioned photographs and following observations, measurements and values describe plants grown during the winter and early spring in 16.5-cm containers in a polyethylene-covered greenhouse in Encinitas, Calif. and under cultural conditions which closely approximate Zonal Geranium commercial production. During the production of the plants, day temperatures averaged 24° C., night temperatures averaged 16° C. and light levels averaged 4,000 foot-candles. Plants were 17 weeks old when the photographs and the description were taken. In the detailed description, color references are made to The Royal Horticultural Society Colour Chart, 2007 Edition, except where general terms of ordinary dictionary significance are used.

Botanical classification: *Pelargonium×hortorum* 'Oglger7049'.

Parentage:

*Female, or seed, parent.*—*Pelargonium×hortorum* 'Pacfox', disclosed in U.S. Plant Pat. No. 18,374.

*Male or pollen parent.*—*Pelargonium×hortorum* 'Fistangoli', disclosed in U.S. Plant Pat. No. 12,274.

Propagation:

*Type*.—By vegetative cuttings.

*Time to initiate roots, summer*.—About ten days at temperatures about 20° C.

*Time to initiate roots, winter*.—About two weeks at temperatures about of 16° C.

*Time to produce a rooted young plant, summer*.—About four weeks at temperatures about 20° C.

*Time to produce a rooted young plant, winter*.—About four weeks at temperatures about 16° C.

*Root description*.—Fine, fibrous; white in color.

*Rooting habit*.—Freely branching; dense.

Plant description:

*Plant and growth habit*.—Upright to outwardly spreading and mounding plant habit; moderately vigorous growth habit.

*Branching habit*.—Freely branching habit with about five primary lateral branches developing per plant, each primary lateral branch with three to four secondary lateral branches; dense and bushy appearance; pinching enhances lateral branch development.

*Plant height, to top of umbels*.—About 34 cm.

*Plant height, to top of foliar plane*.—About 24 cm.

*Plant diameter* (*spread*).—About 45 cm by 48 cm.

*Lateral branches*.—Length: About 19 cm. Diameter: About 1.2 cm. Internode length: About 3 cm. Texture: Pubescent; minute. Strength: Strong. Color: Close to 146C.

Foliage description:

*Arrangement*.—Alternate; simple.

*Length*.—About 8.8 cm.

*Width*.—About 10.5 cm.

*Shape*.—Reniform.

*Apex*.—Rounded.

*Base*.—Cordate.

*Margin*.—Broadly crenate.

*Venation pattern*.—Palmate, reticulate.

*Texture, upper and lower surfaces*.—Pubescent.

*Color*.—Developing leaves, upper surface: Close to N137A. Developing leaves, lower surface: Close to 147C. Fully expanded leaves, upper surface: Close to 137B; venation, close to 137B. Zonation pattern: Location: At leaf surface margin. Width: About 2.3 cm. Color: Close to N137A. Fully expanded leaves, lower surface: Close to 147B; venation, close to 147C.

*Petiole*.—Length: About 5.7 cm. Diameter: About 3 mm. Texture, upper and lower surfaces: Pubescent. Color, upper and lower surfaces: Close to 146B.

Flower description:

*Flower arrangement*.—Round semi-double flowers arranged in hemispherical to nearly spherical umbels arising from apical leaf axils; umbels displayed above and beyond the foliar plane on strong peduncles; umbels upright and flowers face upright or outwardly.

*Fragrance*.—None detected.

*Quantity of flowers*.—Freely flowering habit; about 30 flowers per umbel and about 18 umbels per plant at one time.

*Flowering season*.—In California, flowering is continuous during the spring and summer.

*Flower longevity*.—Individual flowers last about five to seven days on the plant; flowers persistent.

*Umbel height*.—About 7.2 cm.

*Umbel diameter*.—About 8.7 cm.

*Flower diameter*.—About 4 cm.

*Flower depth* (*height*).—About 1.8 cm.

*Flower buds*.—Length: About 1.8 cm. Diameter: About 1.2 cm. Shape: Oval. Color: Close to 61A.

*Petals*.—Quantity per flower and arrangement: Typically eight to nine in about two whorls. Length: About 2 cm. Width: About 2.4 cm. Shape: Obovate. Apex: Rounded. Base: Acute. Margin: Entire. Texture, upper and lower surfaces: Smooth, glabrous; velvety. Color: When opening, upper surface: Close to 64A. When opening, lower surface: Close to 64B. Fully opened, upper surface: Close to 67A; three petals, towards the base, close to 50A; venation, close to 67A; color does not fade with development. Fully opened, lower surface: Close to 67B; venation, close to 67B; color does not fade with development.

*Petaloids*.—Quantity per flower and arrangement: Typically two or three central to the whorls of petals. Length: Variable, about 7 mm to 13 mm. Width: Variable, about 2 mm to 4 mm. Shape: Variable, somewhat distorted. Apex: Rounded. Base: Acute. Margin: Entire, twisted. Texture, upper and lower surfaces: Smooth, glabrous; velvety. Color: When opening and fully opened, upper surface: Close to 67A. When opening and fully opened, lower surface: Close to 67B.

*Sepals*.—Quantity per flower: Typically five arranged in a single whorl. Length: About 1.7 cm. Width: About 4 mm. Shape: Elliptical. Apex: Acuminate. Base: Truncate. Margin: Entire. Texture, upper surface: Smooth, glabrous. Texture, lower surface: Pubescent; minute. Color, upper surface: Close to 146D. Color, lower surface: Close to 146C.

*Peduncle* (*umbel stem*).—Length: About 17 cm. Diameter: About 4 mm. Angle: About 45° from stem axis. Strength: Strong. Texture: Pubescent; minute. Color: Close to 146B.

*Pedicel* (*individual flower stem*).—Length: About 2.5 cm. Diameter: About 1.5 mm. Angle: About 25° to 45° from peduncle axis. Strength: Strong. Texture: Pubescent; minute. Color: Close to 146C tinted with close to 183C.

*Reproductive organs*.—Androecium: Stamen quantity per flower: About five. Filament length: About 5 mm. Filament color: Close to NN155D. Anther length:

About 2 mm. Anther shape: Oblong. Anther color: Close to 51C. Pollen amount: Moderate. Pollen color: Close to 172C. Gynoecium: Pistil quantity per flower: One. Pistil length: About 1 cm. Stigma shape: Five-parted, star-shaped. Stigma color: Close to 61A. Style length: About 2 mm. Style color: Close to 64D. Ovary color: Close to 191A.

*Seeds and fruits*.—Seed and fruit development have not been observed on plants of the new Zonal Geranium.

Disease & pest resistance: Plants of the new Zonal Geranium have not been observed to be resistant to pathogens and pests common to Zonal Geranium plants.

Temperature tolerance: Plants of the new Zonal Geranium have been observed to tolerate temperatures ranging from about 1° C. to about 35° C.

It is claimed:

1. A new and distinct Zonal Geranium plant named 'Oglger7049' as illustrated and described.

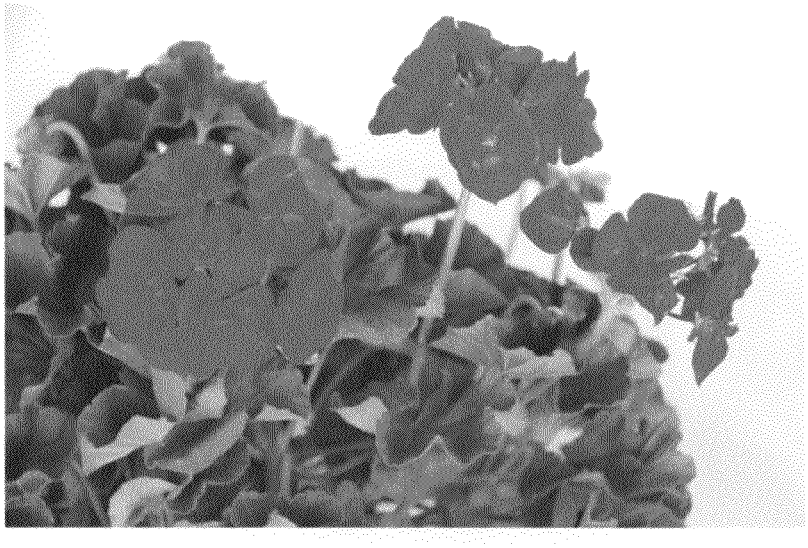
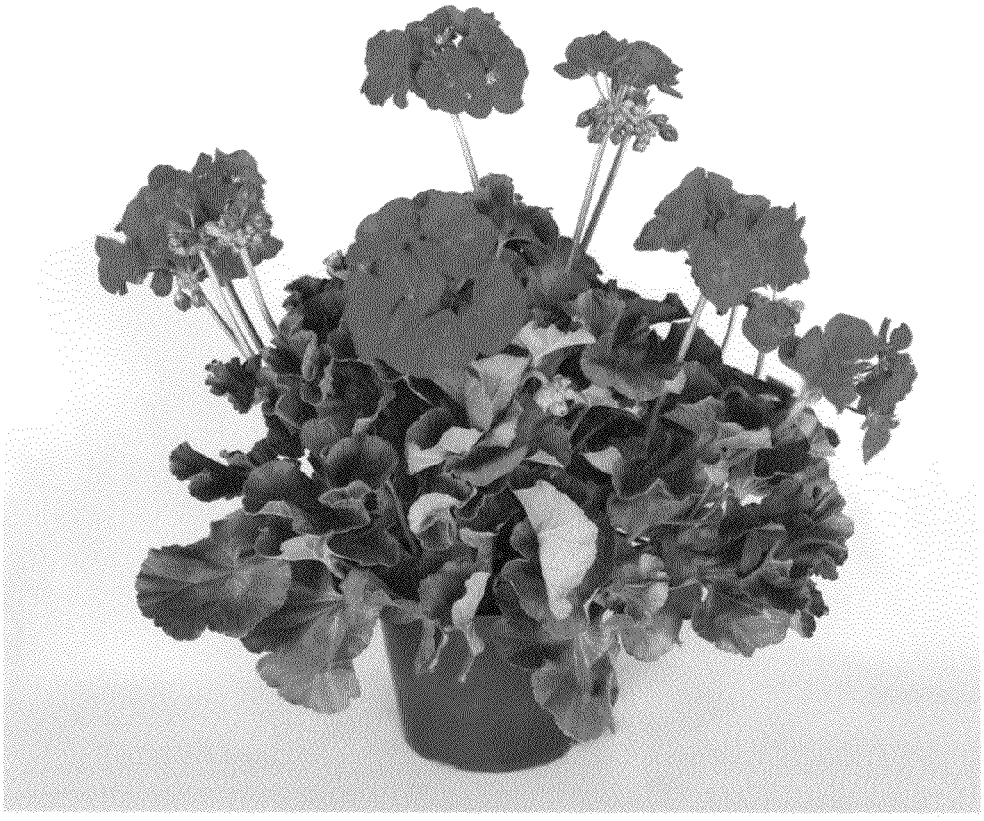

* * * * *